United States Patent
Riley et al.

(10) Patent No.: US 7,871,582 B2
(45) Date of Patent: Jan. 18, 2011

(54) MEDICAL INSTRUMENT CONTAINER SYSTEM

(75) Inventors: Edward D. Riley, Auburn, ME (US); Gary T. Dane, Webster, NH (US)

(73) Assignee: Symmetry Medical USA, Warsaw, IN (US)

( * ) Notice: Subject to any disclaimer, the term of this patent is extended or adjusted under 35 U.S.C. 154(b) by 468 days.

(21) Appl. No.: 11/846,076

(22) Filed: Aug. 28, 2007

(65) Prior Publication Data

US 2008/0116095 A1 May 22, 2008

Related U.S. Application Data

(63) Continuation-in-part of application No. 11/369,428, filed on Mar. 7, 2006.

(51) Int. Cl.
*A61L 2/00* (2006.01)
*A61L 9/00* (2006.01)

(52) U.S. Cl. .................. 422/300; 422/292; 422/297

(58) Field of Classification Search .................. 24/455, 24/456, 457; 40/666; 206/159, 341, 342; 422/300

See application file for complete search history.

(56) References Cited

U.S. PATENT DOCUMENTS

| | | | | |
|---|---|---|---|---|
| 3,704,906 A | * | 12/1972 | Abercrombie | 292/247 |
| 4,157,145 A | | 6/1979 | Jordan | |
| 4,292,749 A | * | 10/1981 | Thomas | 40/308 |
| 4,478,344 A | | 10/1984 | Rehrig | |
| 4,834,125 A | * | 5/1989 | Insalaco | 134/201 |
| 4,887,747 A | * | 12/1989 | Ostrowsky et al. | 222/556 |
| 5,384,103 A | * | 1/1995 | Miller | 422/310 |
| 5,424,048 A | | 6/1995 | Riley | |
| 5,540,901 A | * | 7/1996 | Riley | 422/300 |
| 5,660,784 A | | 8/1997 | Cruce et al. | |
| 5,681,539 A | | 10/1997 | Riley | |
| 5,840,261 A | * | 11/1998 | Monch | 422/300 |
| 5,918,740 A | * | 7/1999 | Berry, Jr. | 206/369 |
| 5,938,899 A | | 8/1999 | Forand | |
| 6,161,718 A | * | 12/2000 | Monbo | 220/486 |
| 6,193,932 B1 | | 2/2001 | Wu et al. | |
| 6,217,835 B1 | | 4/2001 | Riley et al. | |
| 6,331,280 B1 | | 12/2001 | Wood | |
| 6,389,656 B1 | * | 5/2002 | Pellikaan | 24/326 |
| 6,599,482 B1 | * | 7/2003 | Dorin et al. | 422/104 |
| D481,179 S | * | 10/2003 | Wendt et al. | D32/3 |
| 6,789,828 B1 | * | 9/2004 | Borg | 294/87.2 |

(Continued)

OTHER PUBLICATIONS

U.S. Appl. No. 60/709,238.*

(Continued)

*Primary Examiner*—Elizabeth L McKane
*Assistant Examiner*—Regina Yoo
(74) *Attorney, Agent, or Firm*—Hayes Soloway P.C.

(57) ABSTRACT

The system contains a molded plastic reticulated tray composed of a continuous rib that forms a tray rim and a plurality of intersecting ribs defining relatively large openings therebetween. The intersecting ribs are dished and having opposite ends connected to the continuous rib at spaced apart locations therealong. The plurality of intersecting ribs have rounded surfaces so that a fluid sterilant directed at the plurality of intersecting ribs from the outside, upon flowing through said openings, will follow and intimately contact said rounded surfaces to the tray interior so that those surfaces are cleaned thoroughly.

15 Claims, 6 Drawing Sheets

U.S. PATENT DOCUMENTS

2005/0019237 A1 * 1/2005 Riley .......................... 422/297
2005/0163686 A1 7/2005 Bettenhausen et al.
2007/0009408 A1 1/2007 Riley
2007/0039904 A1 * 2/2007 Purushothaman .......... 211/41.8

OTHER PUBLICATIONS

U.S. Appl. No. 60/709,238, Purushothanman, B.; Aug. 18, 2005.*
Ashwani Diagnostics: Medical and Surgical Equipment, http://www.ademcoindia.com/scientific-industrial-lab-equipment/autoclave/sterilizer-pressure.htm, Jan. 11, 2006.

* cited by examiner

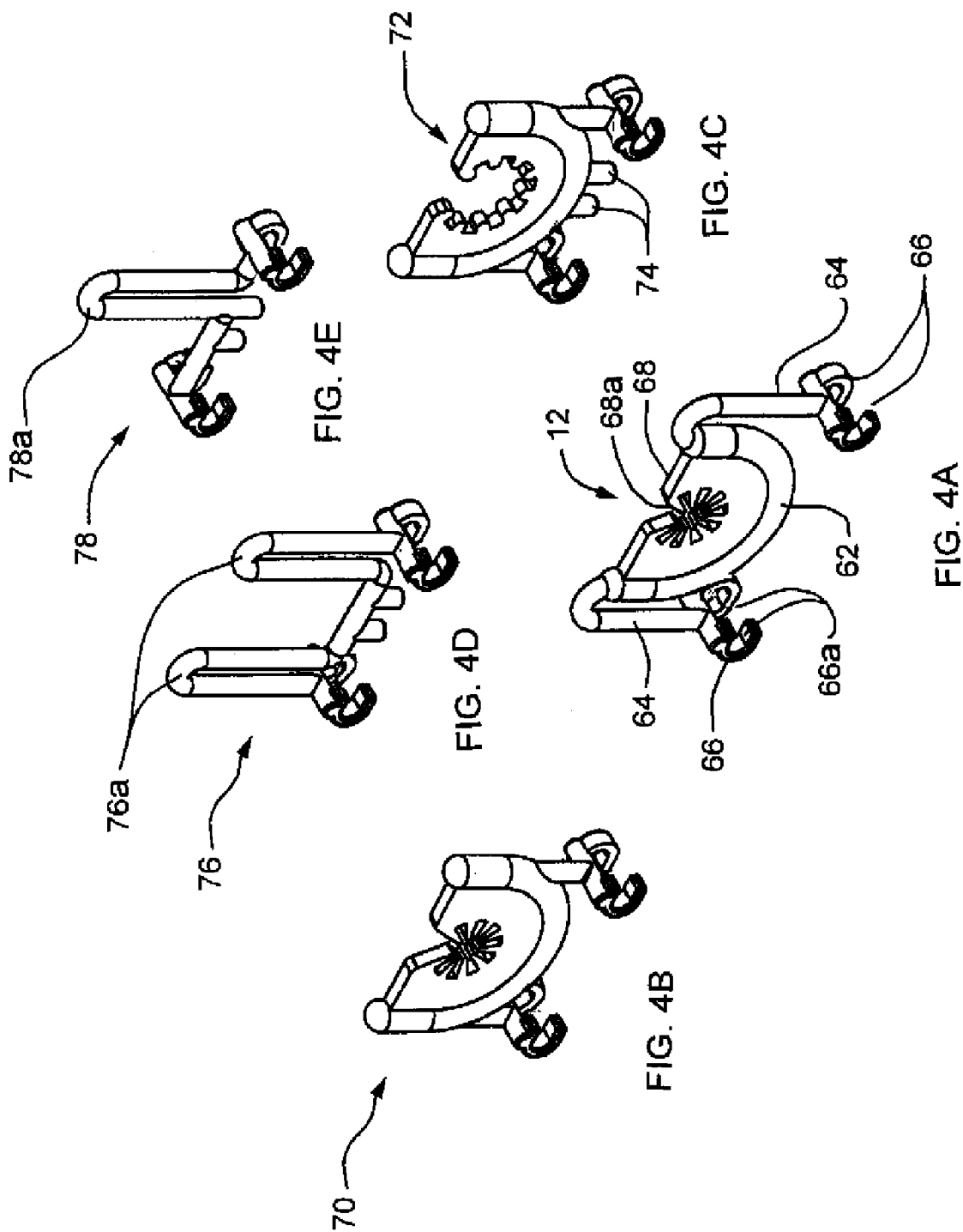

MEDICAL INSTRUMENT CONTAINER SYSTEM

CROSS-REFERENCE TO RELATED APPLICATION

This application claims priority to copending U.S. Application entitled, "Medical Instrument Container System," having Ser. No. 11/369,428 filed Mar. 7, 2006, which is entirely incorporated herein by reference.

FIELD OF THE INVENTION

The present invention is generally related to a system for holding selected medical instruments and devices during sterilization and storage prior to use and to facilitate their cleaning and storage following such use.

BACKGROUND OF THE INVENTION

Different surgical procedures require the use of different sets of instruments or devices, the number of tools in the set depending upon the complexity of the procedure. Thus, prior to a particular procedure, a surgeon determines or knows from experience which instruments will be required. Those instruments are gathered together as a set, placed in a container, which is packaged in a plastic package and sterilized in an autoclave. The packed instruments are then stored in that sterile condition until ready for use. When the surgeon is ready to perform the procedure, the container is brought to the operating room and opened, exposing the still sterile instruments therein. Following use, the instruments are usually returned to the container and sent to a cleaning facility where the containers and instruments therein are placed in a washing machine which directs jets of water/detergent cleaning fluid at the containers and their contents to clean them prior to another sterilization.

To improve the circulation of cleaning fluid throughout the container, the container walls may be formed with a multiplicity of vent holes which may be used to anchor the various brackets which support and fixate the various instruments within the container. Examples of such containers are disclosed in U.S. Pat. Nos. 5,424,048; 5,681,539; 6,193,932 and 6,331,280.

Heretofore, the various containers and trays used for the above purposes have structures whose walls are more closed than open. In other words, the containers have planar walls with a multiplicity of vent holes therein leaving relatively wide webs of plastic extending between the vent holes, the total area of the webs invariably being much larger than the total area of the vent holes in order to maintain the structural integrity and rigidity of the container. As a result, when water/detergent or other cleaning fluid impinges upon the container during the cleaning process, the fluid may not come into intimate contact with all the inside surfaces of the webs with the result that those surfaces will not be cleaned to the extent that they should be. That is, as the cleaning fluid is directed into the container through the vent holes, turbulent flow occurs causing the fluid to flow past portions of the flat interior surfaces between the holes resulting in a shadow effect thereon and insufficient cleaning of the flat surface portions within those shadows.

In order to obtain a better circulation of cleaning fluid through the container during washing, it has been contemplated to use a more open structure for the container, i.e. one composed of intersecting ribs wherein the total area of the openings into the container between the ribs totals much more than that of the ribs bounding the openings. Thus it has been contemplated to form a tray or container of metal wire coated with a plastic material, i.e. similar to a dishwasher rack. Although such an open structure composed of intersecting ribs allows maximum circulation of fluid through the container with minimal shadow effect, it is not particularly suitable for medical applications. During normal usage over time, a plastic coating can be scratched or otherwise damaged by medical instruments, exposing the underlying metal wire, which will oxidize and provide sites for the buildup of bacteria. Also when such a wire structure is deformed, it will tend to remain so with the result that it may not inter-fit properly with other components of the container system. For example, if a wire tray is deformed, its cover may not fit properly on the tray.

Of course, the above problems can be avoided by molding the container or tray entirely of plastic as has been done for clothes baskets, soap dishes and the like. However, such molded plastic open structures are constituted of intersecting webs or ribs, which are thin and have a rectangular cross section. The containers of this type are not rigid enough to protect sensitive medical instruments. Also, since the inner and outer surfaces of those ribs are flat, they suffer the same shadow effect discussed above in connection with perforated plastic trays, albeit to a lesser extent. While the former problem can perhaps be alleviated by thickening the ribs, the latter problem cannot.

Thus it would be very advantageous if there existed a container for holding medical instruments during washing and cleaning processes which has the advantages of plastic coated metal wire baskets in terms of strength and rigidity and none of the aforesaid disadvantages thereof.

SUMMARY OF THE INVENTION

Embodiments of the present invention provide a system and method for retaining medical instruments for sterilization. Briefly described, in architecture, one embodiment of the system, among others, can be implemented as follows. The system contains a molded plastic reticulated tray composed of a continuous rib that forms a tray rim and a plurality of intersecting ribs defining relatively large openings therebetween. The intersecting ribs are dished and having opposite ends connected to the continuous rib at spaced apart locations therealong. The plurality of intersecting ribs have rounded surfaces so that a fluid sterilant directed at the plurality of intersecting ribs from the outside, upon flowing through said openings, will follow and intimately contact said rounded surfaces to the tray interior so that those surfaces are cleaned thoroughly.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 4A to 4E are perspective views of various instrument holders that may be part of the medical instrument container system of FIG. 1, in accordance with the first exemplary embodiment of the present invention.

DETAILED DESCRIPTION

Figure 1:
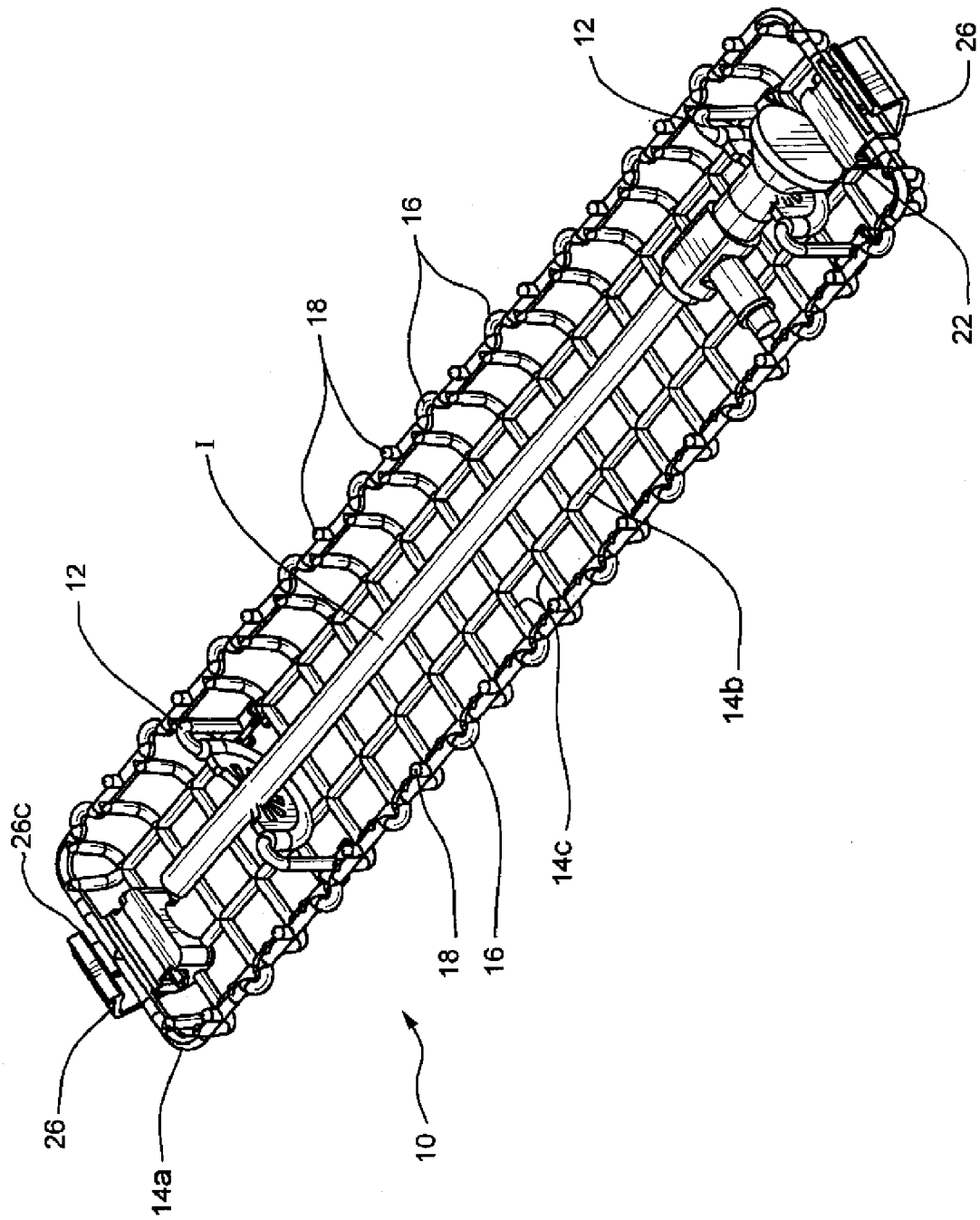
FIG. 1 is perspective view of a medical instrument container system, in accordance with a first exemplary embodiment of the present invention.

FIG. 1 is perspective view of a medical instrument container system, in accordance with a first exemplary embodiment of the present invention. The medical instrument container system comprises a tray 10 which may contain one or more medical instruments or devices I. While the illustrated tray 10 is rectangular, it could just as well have some other shape (e.g., round or oval). Preferably, each medical instrument I is supported within the tray 10 by one or more holders 12 which fix the position of the medical instrument I within the tray 10.

Figure 2:
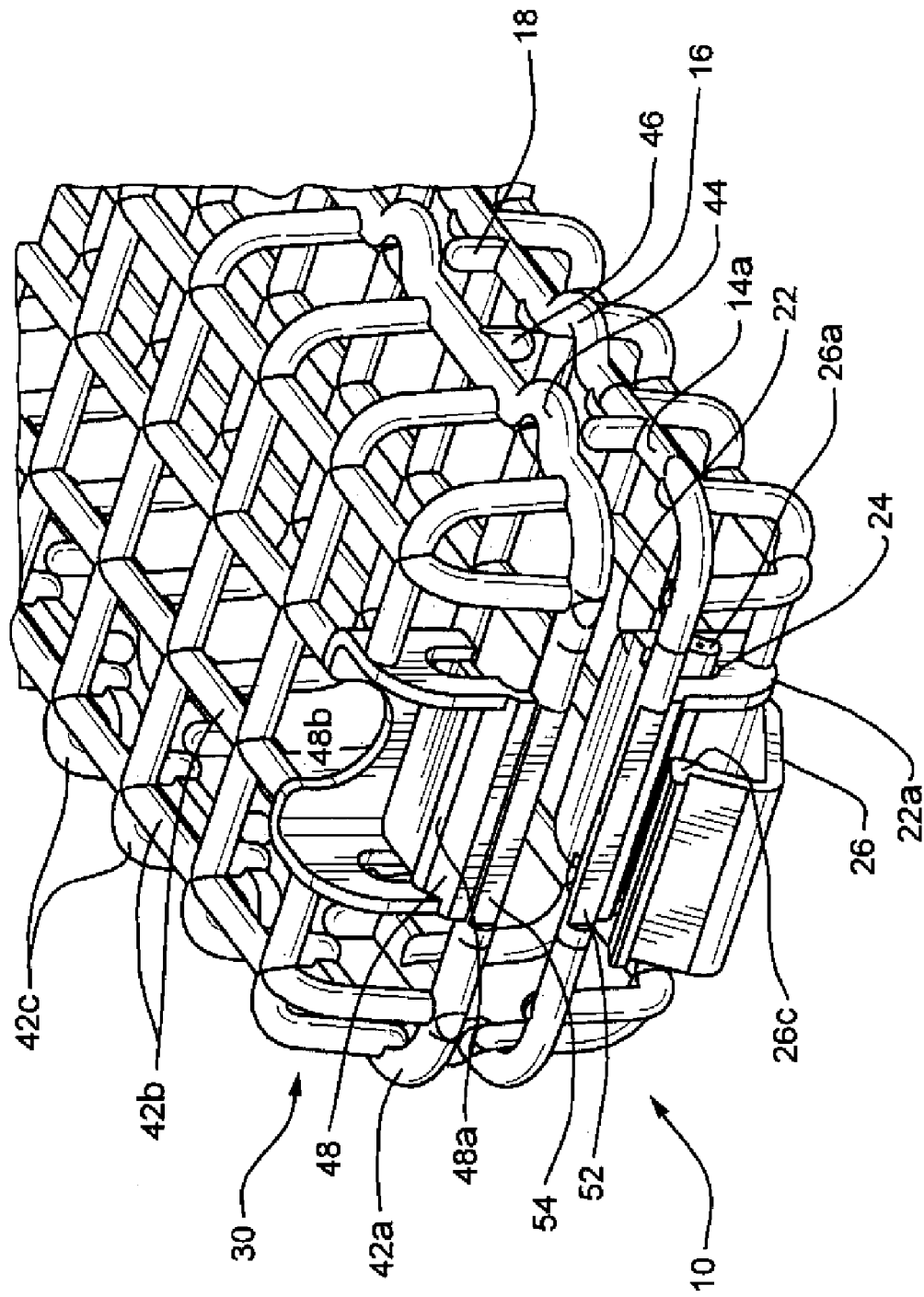
FIG. 2 is a fragmentary perspective view of the medical instrument container system of FIG. 1, in accordance with the first exemplary embodiment of the present invention.

As shown in FIGS. 1 and 2, the tray 10 is a reticulated structure molded entirely of a rigid plastic that is able to withstand cleaning and sterilization processes (e.g., polyphenylsulphone, PTFE, etc.). Thus, the tray 10 is composed of a plurality of spaced-apart ribs 14a, 14b, 14c. The ribs 14a, 14b, 14c include at least one rectangular rib 14a which forms a hoop at the rim of the tray 10, a plurality of spaced-apart, parallel, longitudinal ribs 14b which form a bottom wall of the tray 10 and a multiplicity of spaced-apart, parallel, transverse ribs 14c which intersect the longitudinal ribs 14b at the bottom of the tray 10. The opposite end segments of the longitudinal ribs 14b and the transverse ribs 14c are bent up and connect to the rectangular rib 14a at the inboard face of the rectangular rib 14a at spaced-apart locations therealong. These bent up segments form the sides and ends of the tray 10. Preferably, the longitudinal ribs 14b and the transverse ribs 14c are spaced an appreciable distance from their neighboring parallel ribs 14b, 14c (e.g., 0.75 inch or more), so that the openings between the parallel ribs 14b, 14c are quite large compared to the parallel ribs 14b, 14c themselves. The total area of the tray openings O may be at least twice the total longitudinal sectional area of the longitudinal ribs 14b and the transverse ribs 14c. Also, the ribs 14a, 14b, 14c may be rounded or, more precisely, may have circular cross-sections.

The rectangular rib 14a may be formed with a plurality of outward bends or loops 16 which are spaced along a length of the rectangular rib 14a at the sides of the tray 10. Also, short locating pins 18 may extend up from rectangular rib 14a between the loops 16.

FIG. 2 is a fragmentary perspective view of the medical instrument container system of FIG. 1, in accordance with the first exemplary embodiment of the present invention. Attached to the ribs 14a, 14b, 14c at the opposite ends of container 10 is a pair of fixtures 22. Each of the fixtures 22 may be molded integrally with the rectangular rib 14a and perhaps also the longitudinal ribs 14b and the transverse ribs 14c. However, the fixture 22 may also be designed as a separate part, which can snap onto one or more of those ribs 14a, 14b, 14c. Each fixture 22 may include a pair of laterally spaced-apart ears 22a formed with holes 24 that provide journal bearings for loosely receiving laterally extending axles 26a of a latch member 26.

Figure 3:
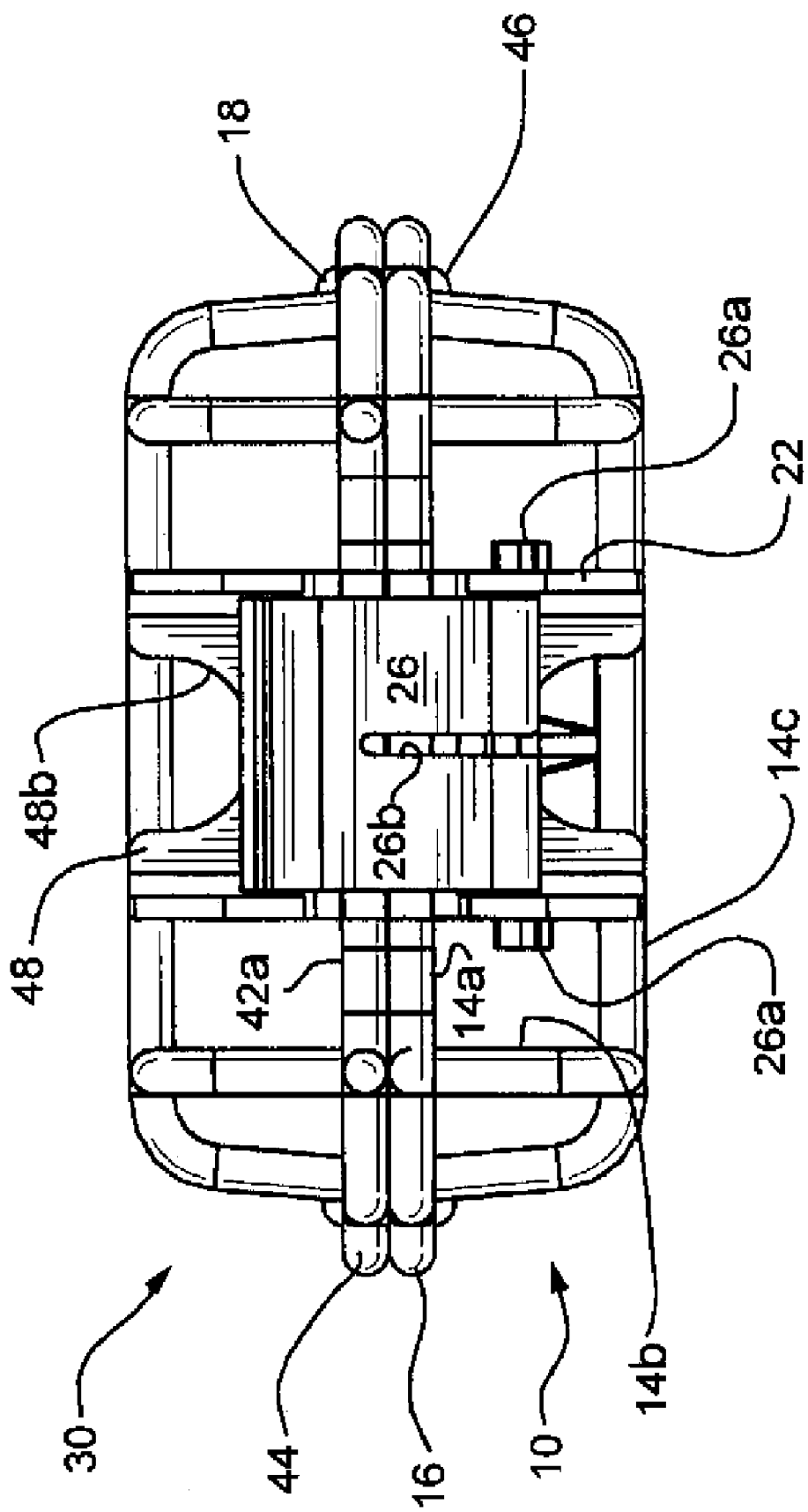
FIG. 3 is an end view of the medical instrument container system of FIG. 1, in accordance with the first exemplary embodiment of the present invention.

FIG. 3 is an end view of the medical instrument container system of FIG. 1, in accordance with the first exemplary embodiment of the present invention. Each of the latch members 26 may have a slit 26b between, and extending perpendicular to, its axles 26a so that the sides of the latch member 26 may be pressed together to permit the insertion of the axles 26a into the holes 24 of the corresponding fixture 22 to facilitate the assembly of the latch members 26 to the fixtures 22. When assembled, each latch member 26 may be manipulated between an open or unlatched position, shown in FIGS. 1 and 2 wherein a latching surface 26c of the latch member 26 is spaced away from the rectangular rib 14a of the tray 10, and a closed or latched position wherein the latching surface 26c is spaced above the rectangular rib 14a a distance slightly less than a diameter of the rectangular rib 14a.

As shown in FIGS. 2 and 3, the container system may also includes a mating molded plastic reticulated cover or lid 30. While the cover 30 and tray 10 may have different depths to minimize molding costs, the illustrated cover 30 is shaped comparably to tray 10. The cover 30 includes a rectangular rib 42a, similar to the rectangular rib 14a of the tray 10, which overlies the rectangular rib 14a of the tray 10 when the cover 30 is positioned on the tray 10 as shown in FIG. 3. The cover 30 also includes a plurality of longitudinal ribs 42b, similar to the longitudinal ribs 14b of the tray 10, as well as a multiplicity of transverse ribs 42c, comparable to the transverse ribs 14c of the tray, which intersect the longitudinal ribs 42b of the cover 30, thereby forming a top wall of the cover 30. The longitudinal ribs 42b and the transverse ribs 42c of the cover 30 are turned down at their ends so that they connect to the rectangular rib 42a of the cover 30 at spaced-apart locations along that rim at the inboard side thereof.

As is the case with the tray 10, the rectangular rib 42a of the cover 30, which forms a rim of the cover 30, is formed with a series of outward bends or loops 44 at spaced-apart locations at the sides of cover 30, as well as a series of locating pins 46 comparable to the pins 18 of tray 10. The respective locating pins 18, 46 and loops 16, 44 on the tray 10 and the cover 30 are positioned so that when the cover 30 is inverted and positioned on the tray 10, the locating pins 18 of the tray 10 project up into the loops 44 of the cover 30 and the locating pins 46 of the cover 30 extend down into the loops 16 of the tray 10 thereby maintaining the tray 10 and the cover 30 in register.

As seen in FIGS. 2 and 3, cover 30 also includes integrally molded fixtures 48 at the opposite ends of the cover 30, which are comparable to the fixtures 22 of tray 10. However, the fixtures 48 of the cover 30 do not form hinges. Rather, the fixtures 48 of the cover 30 function as keepers for the latch members 26 when the cover 30 is positioned on the tray 10 and secured thereto by latch members 26. More particularly, each of the fixtures 48 of the cover 30 (as well as each of the fixtures 22 of the tray 10) is formed with a raised keeper surface 48a. When the corresponding latch member 26 is moved to its latching position, shown in FIG. 3, the latching surface 26c of each latch member 26 resiliently engages and snaps over the keeper surface 48a of the corresponding fixture 48 thereby clamping the cover 30 to the tray 10. When so clamped together, the cover 30 and the tray 10 make line contact along the rectangular ribs 14a, 42a, minimizing the likelihood of bacterial build up where the cover 30 meets the tray 10.

It may be observed from the figures, before assembly of the latch members 26 to the tray 10, the cover 30 is identical to the tray 10 in the first exemplary embodiment. Therefore, the cover 30 and the tray 10, according the first exemplary embodiment, can be made using the same mold. The locating loops 16, 44 and the locating pins 18, 46 may be positioned so that when the cover 30 is inverted and its rectangular rib 42a is brought into register with the rectangular rib 14a of the tray 10, the pins 18 of the tray 10 will project up into the loops 44 of the cover 30 and the pins 46 of the cover 30 will project down through the loops 16 of the tray 10. Furthermore, this applies for both end-to-end registrations of the cover 30 with the tray 10. In other words, if the cover 30 is turned 180° relative to the tray 10, the various locating loops 18, 46 and pins 16, 44 will still inter-fit to bring the cover 30 and tray 10 into register, according to the first exemplary embodiment of the present invention.

As seen in FIG. 3, to enable one to grasp a top of latch member 26 to pull is the latch member 26 away from the end of the cover 30 and to release the latch member 26 from the fixture 48 of the cover 30, the fixture 48 of the cover 30 is formed with a finger notch 48b. A comparable notch may be present in the fixture 22 of the tray 10 to allow the fixtures 22, 48 to remain substantially identical. Also, to provide clearance for each latch member 26 when that latch member 26 is moved to its latching position, the rectangular ribs 14a, 42a may be provided with flats 52, 54, respectively, which face the corresponding latch member 26 as seen in FIG. 2.

It may be a feature of this invention that the molded plastic reticulated tray 10 and cover 30 construction described herein provides a container system which is strong and rigid and able to protect the instruments in the tray 10. Yet, the container system is still very open in that the total longitudinal sectional area of the ribs 14a, 14b, 14c, 42a, 42b, 42c is a relatively small percentage of the total area of the openings in the tray 10 and the cover 30. That coupled with the fact that the surfaces of the ribs 14a, 14b, 14c, 42a, 42b, 42c are rounded, assures that a cleaning fluid directed toward the tray 10 or cover 30 will pass easily into and through those container components, following the streamlined contours of the ribs 14a, 14b, 14c, 42a, 42b, 42c so that there is limited shadow effect at interior surfaces of the container. This construction provides that the entire container system and its contents will be more thoroughly washed or otherwise cleaned in an efficient amount of time.

FIGS. 4A to 4E are perspective views of various instrument holders 12, 70, 72, 76, 78 that may be part of the medical instrument container system of FIG. 1, in accordance with the first exemplary embodiment of the present invention. The first instrument holder 12, shown in FIG. 4A, is a molded plastic part including a generally U-shaped base 62. Opposing ends of the U-shaped base 62 are turned outward and downward to form a pair of spaced-apart vertical legs 64, which extend down below the U-shaped base 62 and are terminated at a pair of quasi-hemispherical clips 66. Each quasi-hemispherical clip 66 has one or more interior clamping surfaces 66a which are dimensioned to frictionally clamp to one or another of the longitudinal ribs 14b and the transverse ribs 14c of the tray 10.

Molded integrally to the U-shaped base 62 is a flexible resilient instrument holding portion 68 formed with a slot 68a for resiliently receiving a medical instrument I, as shown in FIG. 1. The holding portion 68 may be molded integrally with the U-shaped base 62 in the manner described in U.S. patent application Ser. No. 11/299,505, the entire contents of which are hereby incorporated by reference herein. As described in that application, the holding portion 68 is molded integrally with the base 62 so that interstices or crevices or openings between the molded members, which could be possible sites for bacterial infestation, are at least substantially avoided.

As shown in FIG. 1, two of the first instrument holders 12 are clamped to the longitudinal ribs 14b of the tray 10 at opposite sides of tray 10. Accordingly, the first instrument holder 12 may extend substantially the width of the tray 10 to secure the first instrument holders 12 to the outer longitudinal ribs 14b. To anchor the first instrument holders 12 to the tray 10, the quasi-hemispherical clips 66 at the end of one of the vertical legs 64 are engaged to one of the longitudinal ribs 14b of the tray 10 and the vertical legs 64 are spread apart sufficiently so that the quasi-hemispherical clips 66 on the other vertical leg 64 can engage the longitudinal rib 14b at the other side of the tray 10.

The pair of quasi-hemispherical clips 66 on each of the vertical legs 64 face opposing directions. The flexibility of the molded U-shaped base 62 and the vertical legs 64 allow the first instrument holder 12 to be manually twisted such that both quasi-hemispherical clips 66 of the pair can grip the longitudinal ribs 14b and/or the transverse ribs 14c. This arrangement maintains the first instrument holder 12 rigidly in place within the tray 10 more effectively than previously known designs. The vertical legs 64 are sufficiently resilient that, when released, the vertical legs 64 return to unstressed positions, which secure the first instrument holder 12 to the tray 10 and maintain the transverse position of the first instrument holder 12 in the tray 10. The interior clamping surfaces 66a may be molded plastic or flat metal parts, they may have circular cross-sections where they contact the longitudinal ribs 14b and/or the transverse ribs 14c to minimize the contact areas therewith.

Also, the quasi-hemispherical clips 66 may be almost as wide as the distance between the transverse ribs 14c of the tray 10 so that, when secured as aforesaid, the first instrument holder 12 is also longitudinally fixed in the tray 10. Since the openings between the longitudinal ribs 14b and/or the transverse ribs is 14c at the bottom of the tray 10 are substantially square, each first instrument holder 12 could also be turned 90° and clamped to the transverse ribs 14c of tray 10, if that were necessary to retain a particular medical instrument I within the tray 10.

The first instrument holder 12 need not extend the full width of tray 10, as provided in accordance with the first exemplary embodiment. FIG. 4B is perspective view of a second instrument holder 70, which is similar to the first instrument holder 12. The second instrument holder 70 is designed more narrowly than the first instrument holder 12, such that the second instrument holder 70 spans only two openings in the bottom of the tray 10.

FIG. 4C is perspective view of a third instrument holder 72 which is similar to the second instrument holder 70 except that the U-shaped base is formed with a pair of integral depending posts 74 which are spaced apart a distance substantially equal to the diameter of the longitudinal ribs 14b and/or the transverse ribs 14c at the bottom of the tray 10. When the third instrument holder 72 is clipped to the tray 10 in a manner similar to that of the first instrument holder 12, the integral depending posts 74 will straddle one of the longitudinal ribs 14b or the transverse ribs 14c at the bottom of the tray 10, thereby positively fixing a lateral or transverse position of the third instrument holder 72 within the tray 10.

FIG. 4D is a perspective view of a fourth instrument holder 76. The fourth instrument holder 76 has a pair of spaced-apart upstanding loops 76a for fixating a relatively wide instrument or device. FIG. 4E is a perspective view of a fifth instrument holder 78. The fifth instrument holder 78 has a single upstanding loop 78a which may be suitable, for example, to secure a scissor handle or other such instrument having an eye, wherein the eye would be pierced by the single upstanding loop 78a.

Figure 5A:
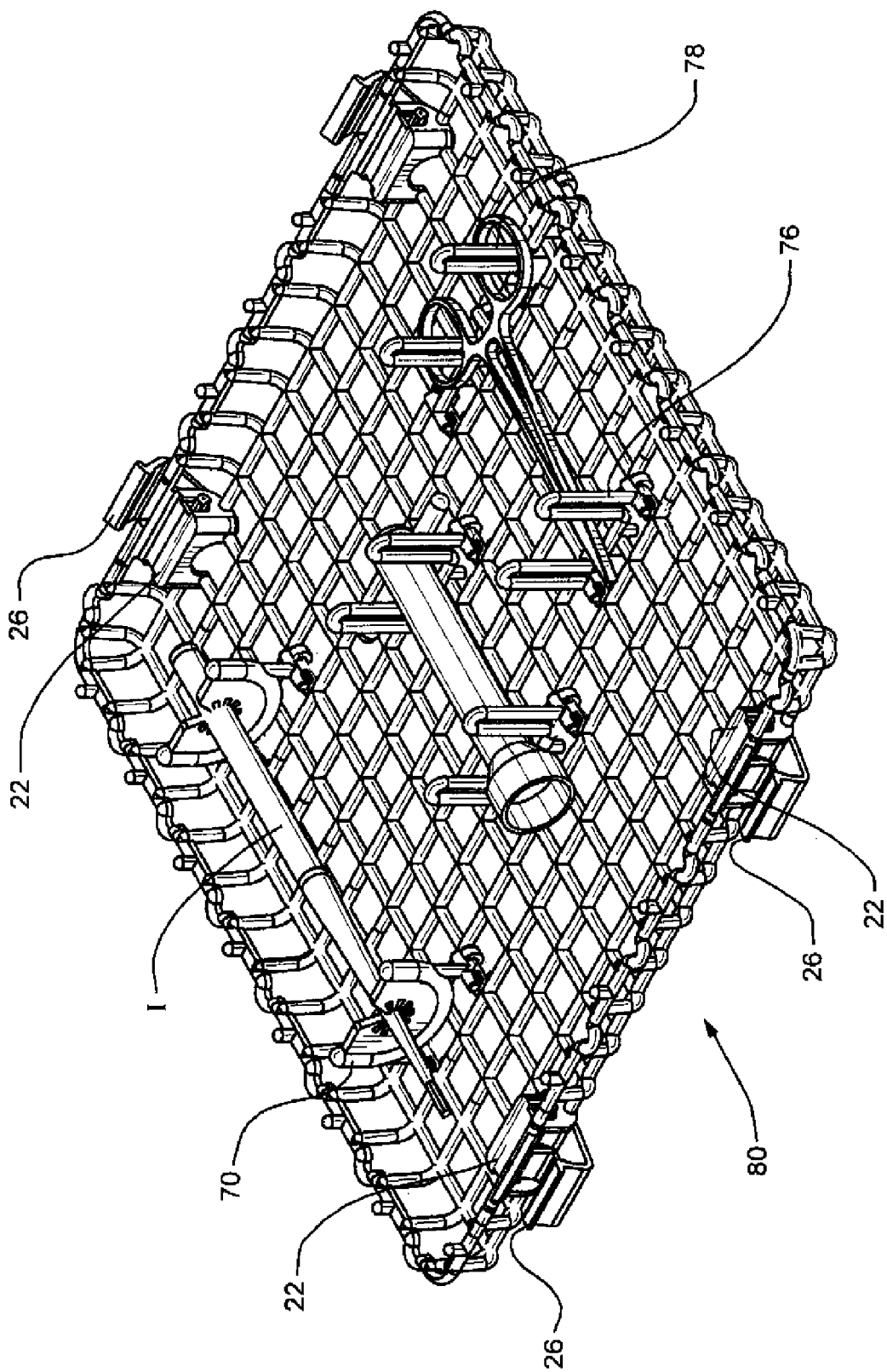
FIG. 5A is perspective view of a medical instrument container system, in accordance with a second exemplary embodiment of the present invention.
Figure 5B:
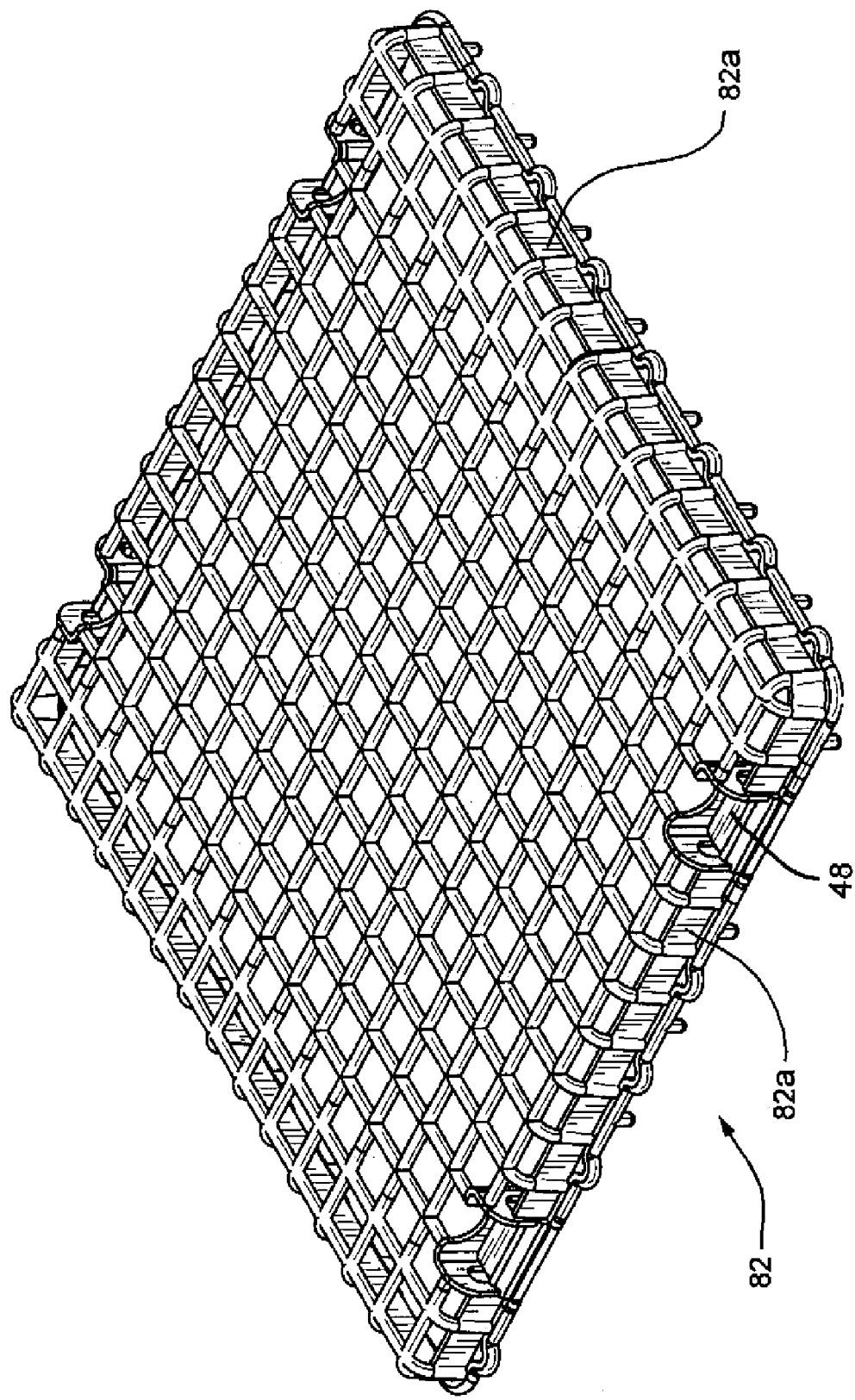
FIG. 5B is a perspective view of a cover of the medical instrument container system shown in FIG. 5A, in accordance with the second exemplary embodiment of the present invention.

FIG. 5A is perspective view of a medical instrument container system, in accordance with a second exemplary embodiment of the present invention. More precisely, a molded plastic reticulated tray 80 is shown in FIG. 5A. FIG. 5B is a perspective view of a cover 82 of the medical instrument container system shown in FIG. 5A, in accordance with the second exemplary embodiment of the present invention. It should be noted, in accordance with the second exemplary embodiment, that the molded plastic reticulated tray 80 and the cover 82 are much wider than the tray 10 and the cover 30 of the first exemplary embodiment. The larger space afforded by the wide tray 80 and cover 82, in combination with a variety of the instrument holders shown in FIGS. 4A to 4E, allows a whole set of instruments or devices to be protectively enclosed for sterilization and handling. Being larger, the tray 80 and cover 82 may be formed with two sets of fixtures 22, 48 and latch members 26. Here also, the tray 80 and the cover 82 may be identically molded plastic parts. However, the cover 82 may be somewhat different from the tray in that the cover 82 may include solid side straps 82a, shown in FIG. 5B, to prevent loose instrument I from sliding out of the tray 80. The latch members 26 are attached to the tray fixtures 22 but not to the cover fixtures 48, with the latter functioning as keepers for the latch members 26. Of course in both the first and second exemplary embodiments, the latch members 26 could just as well be hinged to the cover fixtures 48 with the tray fixtures 22 functioning as keepers for those latch members 26.

It is apparent from the foregoing that the container system of the present invention has definite advantages in terms of protecting the instruments contained therein as well as facilitating efficient washing and sterilization of those instruments as well as the inside surfaces of the container. Yet being molded entirely of plastic, the system can be made in quantity relatively inexpensively. Therefore, it should prove to be very useful in hospital, clinics and other settings where medical instruments and devices have to be cleaned on a routine basis.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The invention claimed is:

1. A container system for medical instruments, the system comprising:
   a molded plastic reticulated tray having a continuous rib that forms a tray rim about a perimeter of the molded plastic tray;
   a tray wall, formed from a plurality of ribs connected to the tray rim, the plurality of ribs having opposite ends connected to the tray rim at spaced apart locations therealong;
   a middle portion of the plurality of intersecting ribs forming a tray base, the tray base having a plurality of perpendicularly intersecting ribs formed from the plurality of ribs, the intersecting ribs having a circular cross-section and central axes configured in a plane, said intersecting ribs being dished and defining openings therebetween whereby a fluid sterilant directed at the plurality of perpendicularly intersecting ribs from the outside, upon flowing through said openings, will follow and contact rounded surfaces to the tray so that those surfaces are cleaned; and
   at least one instrument holder having a pair of resilient legs wherein each of said legs includes a free end terminated by a pair of quasi-hemispherical clips facing opposing directions and releasably engaging said plurality of intersecting ribs.

2. The container system defined in claim 1, wherein the total area of said openings is at least twice the total longitudinal-sectional area of said plurality of intersecting ribs.

3. The container system defined in claim 1, wherein the tray is molded of polyphenylsulphone.

4. The container system defined in claim 1, wherein the tray is generally rectangular and said openings are square.

5. The container system defined in claim 4, wherein the tray includes at least two similar latch fixtures affixed to the continuous rib opposite and facing away from one another, each latch fixture including a journal bearing and a keeper surface.

6. The container system defined in claim 5, and further including a latch member hinged to each latch fixture at the journal bearing thereof.

7. The container system defined in claim 1, and further including a reticulated cover which is a mate to said tray so that when the cover is inverted and positioned with its continuous rim in register with the continuous rim of the tray, the tray and cover make line contact and form a cage.

8. The container system defined in claim 7 and further including means for releasably clamping together the continuous rims of the tray and cover.

9. The container system defined in claim 8, wherein the clamping means comprise a plurality of similar first latch fixtures affixed to the continuous rib of the tray, said first latch fixtures being opposite and facing away from one another, a plurality of second latch fixtures affixed to the continuous rib of the cover, said second latch fixtures being opposite and facing away from one another, each of said latch fixtures including a journal bearing and a keeper surface, said first and second latch fixtures being located directly opposite one another when the continuous ribs of the tray and cover are in register with one another, said opposite latch fixtures constituting a cooperating pair of latch fixtures, and a latch member hinged to one of each cooperating pair of latch fixtures at the journal bearing thereof, each said latch member being adapted to engage the keeper surface of the other latch fixture of each cooperating pair of latch fixtures.

10. The container system defined in claim 1 wherein said plurality of intersecting ribs include a first set of ribs spaced parallel to one another, a second set of ribs spaced parallel to one another, said first and second sets of ribs being orthogonal so that the ribs define rectangular openings.

11. The container system defined in claim 10 wherein said instrument holder is spanning at least one of said openings.

12. The container system defined in claim 11 wherein the length of each clip is slightly less than the side length of each of said openings.

13. The container system defined in claim 11 wherein said instrument holder also includes a plurality of spaced-apart depending posts which are adapted to straddle one of said plurality of intersecting ribs when the instrument holder is releasably engaging said different ones of said plurality of intersecting ribs.

14. The container system defined in claim 1, wherein said pair of quasi-hemispherical clips are aligned along an axis substantially at the center of both of said quasi-hemispherical clips, wherein the axis is positioned substantially perpendicular to an axis aligned with one of each of said legs and substantially perpendicular to a first plane and a second plane, wherein one clip of said pair of quasi-hemispherical clips is located within the first plane and the other clip of said pair of quasi-hemispherical clips is located within the second plane, wherein said first plane is positioned in a different location along said axis than said second plane.

15. The container system defined in claim 1, wherein each of said legs are positioned to be twisted about an axis aligned along a length of one of each of said legs, whereby twisting at least one of said legs displaces said pair of quasi-hemispherical clips from at least one of said plurality of intersecting ribs.

* * * * *